United States Patent [19]

Hancock

[11] Patent Number: 4,704,279

[45] Date of Patent: Nov. 3, 1987

[54] MANUFACTURING A PRODUCT FOR TREATMENT OF THE HUMAN BODY

[76] Inventor: Kenneth A. Hancock, 80 Holbrook Road, Alvaston, Derby, England

[21] Appl. No.: 680,063

[22] Filed: Dec. 10, 1984

[51] Int. Cl.$^4$ .............................................. A61K 35/78
[52] U.S. Cl. .................................. 424/195.1; 424/451; 424/464; 514/825; 514/899
[58] Field of Search ...................... 424/195.1, 451, 464

[56] References Cited

PUBLICATIONS

Lewis Medical Botany, Wiley and Sons, New York, 1977, p. 323.

Primary Examiner—J. R. Brown
Assistant Examiner—John W. Rollins
Attorney, Agent, or Firm—Robert B. Chickering; Glen R. Grunewald

[57] ABSTRACT

A product for treatment of arthritis and migraine is formed from the Feverfew plant. The leaves and part of the stalk are harvested from the *Chrysanthemum parthenium* form of the plant immediately prior to flowering and then freeze dried, milled and converted into capsule or tablet form for human use.

8 Claims, No Drawings

MANUFACTURING A PRODUCT FOR TREATMENT OF THE HUMAN BODY

This invention relates to a method of manufacturing a product for treatment of the human body and the product produced by such manufacture.

Certain herbs are known to have properties which can effectively treat certain human ailments, but it is important when converting a herb into a form suitable for healing use to ensure that the herb is cleansed but retains all its natural properties. Problems have been encountered in this respect resulting in unacceptable forms of the end product being made available for human use. It is also important to identify and use those parts of the herbs which contain all the natural properties so as to ensure that the product manufactured is wholly effective.

According to the present invention there is provided a method of manufacturing a product for treatment of the human body, the method comprising the steps of harvesting the leaves together with an upper part of the stalk from the *Chrysanthemum parthenium* form of the Feverfew plant immediately prior to the flowering of the plant, freeze drying the harvested part of the plant, and converting the freeze dried harvested part of the plant, into a form suitable for treating the human body.

Preferably the upper 40% of the stalk of the plant is harvested together with the leaves.

Preferably also the harvested part of the plant is converted after freeze drying by milling and subsequent encapsulation.

The present invention also provides a product for treatment of the human body manufactured by the method as described in any of the three preceding paragraphs.

An embodiment of the present invention will now be described by way of example only:

The fewerfew herb is used in the manufacture of a product for treating migraine and arthritis but it is only one form of the plant which can result in a product effective for treatment. Additionally the plant should be grown under natural conditions, for example chemical fertilisers should not be used. The form required to be used is *Chrysanthemum* (*Tanacetum* or *Matricania*) *Parthenium*.

The plant is harvested immediately prior to flowering when the buds have just formed and the leaf stem is green and flexible, that is only first year plants may be used for optimum effect. It is the leaves and the upper 40% of the stalk of the plant which are harvested, as those parts of the plant have been identified as containing the concentrated form of these constituents most effective in treatment of migraine and arthritis. As most of the benefit resides in the leaf of the plant it is preferable that in the harvested plant the proportion of leaf to stem is 3 to 1.

The harvested parts of the plant are then dried by being placed in a vacuum chamber and frozen, with the chamber subsequently being evacuated. With such drying by converting the ice directly to water vapour, the low temperatures used prevent denaturation of the various proteins and also reduce losses of volatile oils. The rapid loss of water allows the dried cell walls of the plant to retain a degree of rigidity and freeze dehydrated herbs are very clean. Freeze drying preserves the plant in the most natural condition and prevents spoiling by the growth of bacteria, yeast and moulds which would otherwise occur due to the naturally occurring moisture content of the plants. When the plants are washed and immediately flash-frozen for transport as soon as feasible after harvesting, microbial loads are then less, enzymatic activity is retarded, and cellular structure, colour and flavour are retained.

After freeze drying, the harvested plants are milled before being converted into capsule form by conventional encapsulation techniques.

The use of the Feverfew plant prepared in this way is effective when taken to prevent attacks of migraine. Dosage may be regular. Also use of Feverfew for an arthritic condition will virtually remove pain in a matter of days and the soreness, swelling and inflammation of the joints will decrease after a further period thereby restoring mobility to the joints.

Various modifications may be made without departing from the invention. For example the product may be formed as a tablet rather than a capsule.

In this particular area of activity botanical names are used imprecisely. The herb which is used in the present invention is known correctly and variously as *Chrysanthemum parthenium*, *Tanecetum parthenium* and *Matricania parthenium*. These names are often used incorrectly to describe other Feverfew varieties, for example Corn Feverfew, Golden Feverfew, Sweet Feverfew, and Sea Feverfew. These species should not be used in the present invention.

Whilst endeavouring in the foregoing specification to draw attention to those features of the invention believed to be of particular importance it should be understood that the Applicant claims protection in respect of any patentable feature or combination of features hereinbefore referred to whether or not particular emphasis has been placed thereon.

I claim:

1. A method of preparing a product for relieving symptoms of migraine and arthritis, the method comprising the steps of harvesting the leaves from the *Chrysanthemum partenium* form of the Feverfew plant immediately prior to the flowering of the plant, freeze drying said leaves, milling the resultant freeze dried leaves to be subdivided sufficiently to be enclosed in a capsule and incorporating said milled leaves into a form suitable for treating the human body.

2. A method according to claim 1, wherein the upper 40% of the stalk of the plant is harvested together with the leaves.

3. A method according to claim 2, wherein the harvested proportion of leaf to stalk is 3 to 1.

4. A method according to claim 1, wherein the first year plant is harvested.

5. A method according to claim 1 wherein said form suitable for treating the human body is said milled product enclosed in a capsule.

6. A method according to claim 1 wherein said form suitable for treating the human body is said milled product formed as a tablet.

7. An article comprising milled, subdivided, freeze dried leaves of the *Chrysanthemum partenium* plant enclosed in a capsule.

8. An article comprising milled, subdivided, freeze dried leaves of the *Chrysanthemum partenium* plant in the form of a tablet.

* * * * *